United States Patent [19]

McKinnie et al.

[11] Patent Number: 4,982,002
[45] Date of Patent: Jan. 1, 1991

[54] METHYLTHIO SUBSTITUTED DIAMINOTOLUENES

[75] Inventors: Bonnie G. McKinnie, Magnolia, Ark.; Paul F. Ranken, Baton Rouge, La.

[73] Assignee: Ethyl Corporation, Richmond, Va.

[21] Appl. No.: 379,873

[22] Filed: Jul. 14, 1989

Related U.S. Application Data

[60] Continuation-in-part of Ser. No. 224,017, Jul. 25, 1988, abandoned, which is a continuation of Ser. No. 917,168, Oct. 9, 1986, Pat. No. 4,760,188, which is a continuation-in-part of Ser. No. 783,421, Oct. 3, 1985, abandoned, which is a division of Ser. No. 619,675, Jun. 11, 1984, Pat. No. 4,594,453.

[51] Int. Cl.$^5$ ............................................. C07C 149/42
[52] U.S. Cl. .................................................. 564/440
[58] Field of Search ......................................... 564/440

[56] References Cited

U.S. PATENT DOCUMENTS 4,670,598  6/1987  Davis ............................ 564/335 X Primary Examiner—Robert V. Hines
Attorney, Agent, or Firm—Patricia J. Hogan; Richard J. Hammond

[57] ABSTRACT

3,5-Di(methylthio)-2,6-diaminotoluene is a novel compound which, alone or in admixture with 3,5-di(methylthio)-2,4-diaminotoluene, is particularly useful as a chain extender in the preparation of polyurethanes.

2 Claims, No Drawings

METHYLTHIO SUBSTITUTED DIAMINOTOLUENES

CROSS-REFERENCE TO RELATED APPLICATIONS

This application is a continuation-in-part of application Ser. No. 224,017, filed July 25, 1988, now abandoned; which in turn is a continuation of Ser. No. 917,168, filed Oct. 9, 1986, now U.S. Pat. No. 4,760,188; which is a continuation-in-part of Ser. No. 783,421, filed Oct. 3, 1985, now abandoned; which in turn is a division of Ser. No. 619,675, filed June 11, 1984, now U.S. Pat. No. 4,594,453.

BACKGROUND

As disclosed in U.S. Pat. No. 4,146,688 (Schwindt et al.), it is known that aromatic diamines can be used as chain extenders in the preparation of polyurethanes. However, some aromatic diamines are too reactive with isocyanates to permit proper handling, and it has also been found that some aromatic diamines provide polyurethanes having unsatisfactory physical properties. Another problem apt to be presented by the use of aromatic diamines is that many such compounds are known to be toxic or have a structure such as to make it predictable that, when tested, they will probably prove to be carcinogenic.

SUMMARY OF INVENTION

An object of this invention is to provide a novel aromatic diamine.

Another object is to provide a novel aromatic diamine which is suitable for the preparation of polyurethanes having acceptable physical properties.

A further object is to provide such an aromatic diamine which lacks the toxicological problems of carcinogenic diamines.

These and other objects are attained by the provision of 3,5-di(methylthio)-2,6-diaminotoluene.

DETAILED DESCRIPTION

The substituted diaminotoluene of the invention can be prepared by reacting 2,6-diaminotoluene with methyl disulfide in the presence of a suitable catalyst, such as aluminum chloride, cuprous iodide, etc., at a temperature in the range of about 20–300° C. The 2,6-diaminotoluene used in the reaction may be pure or crude, and it is frequently desirable to employ a commercial mixture of 2,4- and 2,6-diaminotoluenes, such as the 80/20 mixture, as the starting material. The methyl disulfide is generally used in at least the stoichiometric amount, although at least some desired product can be obtained when a lesser amount is employed. The amount of catalyst utilized is a catalytic amount, generally an amount such as to provide a catalyst/diaminotoluene mol ratio of about 0.01–0.5/1, as taught more fully in U.S. Pat. No. 4,594,453 (Ranken et al.), the teachings of which are incorporated herein in toto by reference.

The 3,5-di(methylthio-2,6-diaminotoluene or 3,5-di(methylthio)-2,4-diaminotoluene/3,5-di(methylthio)-2,6-diaminotoluene mixture formed by the reaction is particularly useful as a chain extender in the preparation of polyurethanes. As taught in U.S. Pat. No. 4,595,742 (Nalepa et al.), the teachings of which are incorporated herein in toto by reference, the compound or mixture can be effectively employed for this use without having to be separated from other products of the reaction; and its utilization provides for a suitable pot life and leads to the formation of polyurethanes having acceptable physical properties. The compound and its mixtures with 3,5-di(methylthio)-2,4-diaminotoluene also have the advantage of being toxicologically acceptable.

The following example is given to illustrate the invention and is not intended as a limitation thereof.

EXAMPLE

One molar proportion of a commercial mixture of 80% 2,4-diaminotoluene and 20% 2,6-diaminotoluene was heated with 0.05 molar proportion of cuprous iodide at 150° C. for one hour. Methyl disulfide was then added in sufficient excess to maintain the reaction temperature at 135° C., and the reaction was conducted for 10 hours to achieve 100% conversion of the diaminotoluene mixture. Analysis of the product showed it to contain 5 mol % of mono(methylthio) derivatives of the diaminotoluene mixture and 94 mol % of a mixture of 3,5-di(methylthio)-2,4-diaminotoluene and 3,5-di(methylthio)-2,6-diaminotoluene.

What is claimed is:

1. A mixture of 3,5-di(methylthio)-2,4-diaminotoluene and 3,5-di(methylthio)-2,6-diaminotoluene.

2. The mixture of claim 1 wherein the ratio of 3,5-di(methylthio)-2,4-diaminotoluene to 3,5-di(methylthio)-2,6-diaminotoluene is about 80/20.

* * * * *